United States Patent [19]
Weissman

[11] Patent Number: 6,106,290
[45] Date of Patent: Aug. 22, 2000

[54] DENTAL TOOL WITH CONTROLLED SIMULTANEOUS RECIPROCAL AND OSCILLATING MOTION

[76] Inventor: Bernard Weissman, 225 E. 48th St., New York, N.Y. 10017

[21] Appl. No.: 09/186,526

[22] Filed: Nov. 5, 1998

[51] Int. Cl.[7] .................................................. A61C 1/07
[52] U.S. Cl. .......................................... 433/122; 433/118
[58] Field of Search ................................... 433/122, 118, 433/123, 119

[56] References Cited

U.S. PATENT DOCUMENTS

| 4,781,588 | 11/1988 | Granier | 433/122 |
| 4,976,625 | 12/1990 | Weissman | 433/118 |
| 5,453,008 | 9/1995 | Berlin | 433/122 |

Primary Examiner—John J. Wilson
Attorney, Agent, or Firm—Helfgott & Karas, P C

[57] ABSTRACT

In a dental hand-piece, a sleeve connected to a dental tool reciprocates in a head. A fixed protrusion from the head engages a groove on the moving sleeve. The groove has portions that are transverse to the axis of reciprocation causing the sleeve to oscillate about the axis during reciprocation.

23 Claims, 6 Drawing Sheets

DENTAL TOOL WITH CONTROLLED SIMULTANEOUS RECIPROCAL AND OSCILLATING MOTION

BACKGROUND OF THE INVENTION

The present invention is an improvement on the reciprocating dental tool disclosed in U.S. Pat. No. 4,976,625, issued Dec. 11, 1990, to the present applicant. This patent is hereby incorporated herein by reference.

In the issued U.S. Pat. No. 4,976,625, a hand-piece, including a sleeve slidingly mounted in the head of the hand-piece, is driven by a common dental rotary drill driver, and converts the rotational motion of the driver to reciprocating motion of the sleeve by means of an eccentrically rotating member. The sleeve, having an annular recess within which the eccentric rotates, is reciprocally moved together with a dental tool that is fixedly held in the sleeve or is manufactured integrally with the sleeve.

Rotation of the tool, for example, a file, around its longitudinal axis, that is, around the axis of reciprocation, is prevented by an axially oriented groove on the reciprocating sleeve. A projection from the fixed head of the hand-piece, engages the axial groove so that the tool attached to the sleeve may only translate parallel to the reciprocating axis, but may not rotate randomly around the reciprocating axis.

However, this constraint of tool motion to pure translation can limit the utility of the tool. There are times when controlled rotation of the tool may be extremely valuable and this feature is substantially lost in the U.S. Pat. No. 4,976,625 device, although undesirable random rotation of the tool is prevented.

What is needed is a tool where controlled limited oscillatory motion is combined with controlled, limited reciprocal motion when the tool works in abrading, filing or removing excess materials in the mouth, or, works on other prosthetic devices outside the mouth.

SUMMARY OF THE INVENTION

It is the object of the present invention to provide an improved dental head assembly or hand-piece having a dental tool with combined and controlled reciprocating and oscillating motion.

In a dental hand-piece, a sleeve connected to a dental tool reciprocates in a head. A fixed protrusion from the head engages a groove on the moving sleeve. The groove has portions that are transverse to the axis of reciprocation causing the sleeve to oscillate about the axis during reciprocation.

In an alternative embodiment of a hand-piece in accordance with the invention, there are a plurality of grooves on the surface of the sleeve. This permits a selection by the dental practitioner of angular positions for the sleeve relative to the fixed head.

In a further alternative construction, the plurality of grooves are connected together by a shallow channel that is at a right angle to the axis of reciprocal motion of the sleeve. This channel permits the protrusion from the head to move from channel to channel when higher forces are applied, as when a tool connected to the sleeve tends to jam while acting on a tooth or prosthetic device.

The combined vertical and helical movement facilitates safe access and reach in dental, clinical procedures. This novel movement with appropriate inserts, such as miniature saws for cutting bone sections, provides side clearance that overcomes frictional heat generation and eliminates the cut particles in its upward moving position.

These combined movements of appropriate barbed flexible file instruments clear and widen root canals for creating access to endodontic root canal treatment. The gentle helical movement advances the file incrementally into the canal without ledging or excessive stress, preventing wedging and breakage of files within the canal's confines.

These combined movements are necessary for proper access and for forming interdental in situ anatomical profiles and forms in a great variety of treatments where rotary instrumentation and tools are ineffective and contraindicated.

Further, objects and advantages of the invention will be obvious from the specification.

The invention accordingly comprises the features of construction, combinations of elements, and arrangements of parts which will be exemplified in the constructions hereinafter set forth, and the scope of the invention will be indicated in the claims.

BRIEF DESCRIPTION OF THE DRAWINGS

For a full understanding of the invention, reference is had to the following description taken in connection with the accompanying drawings, in which.

DESCRIPTION OF PREFERRED EMBODIMENTS

Figure 1:
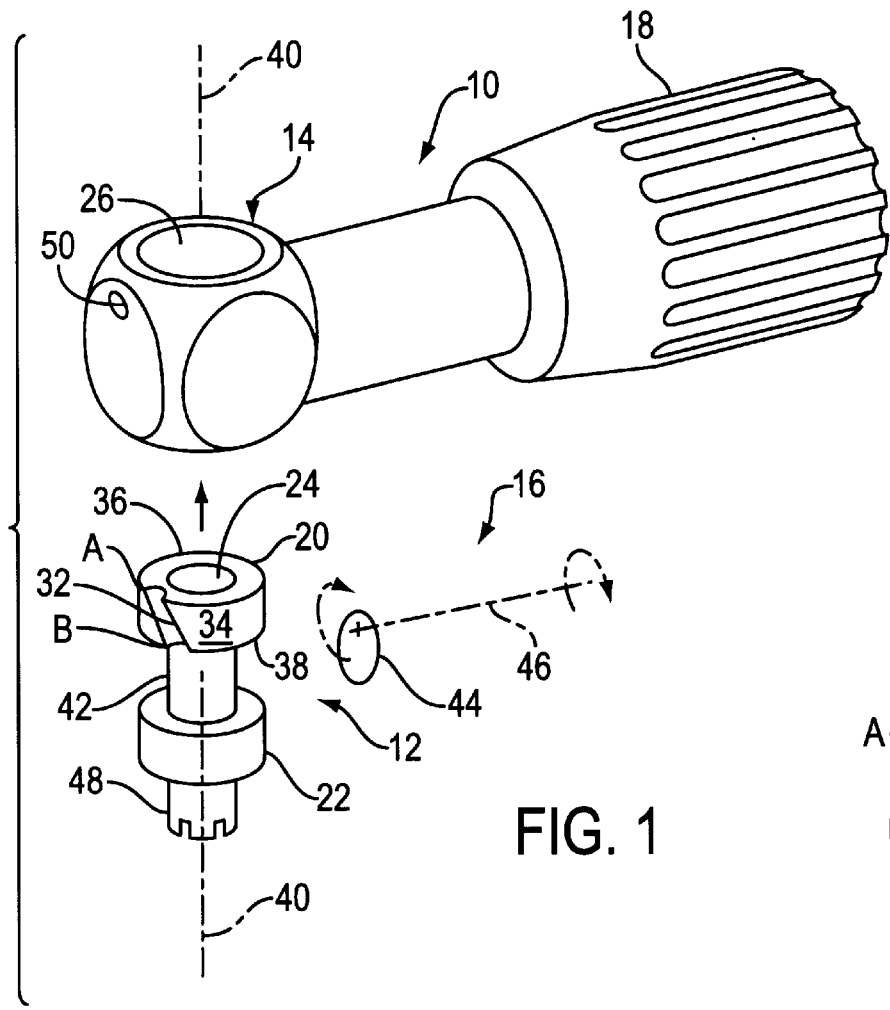
FIG. 1 is a partial exploded view, in perspective, of a driver hand-piece and tool-holding sleeve in accordance with the invention.
Figure 4:
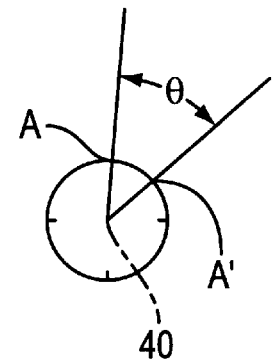
FIG. 4 is a diagram illustrating the oscillatory motion of the sleeve in the device of FIG. 1.
Figure 2:
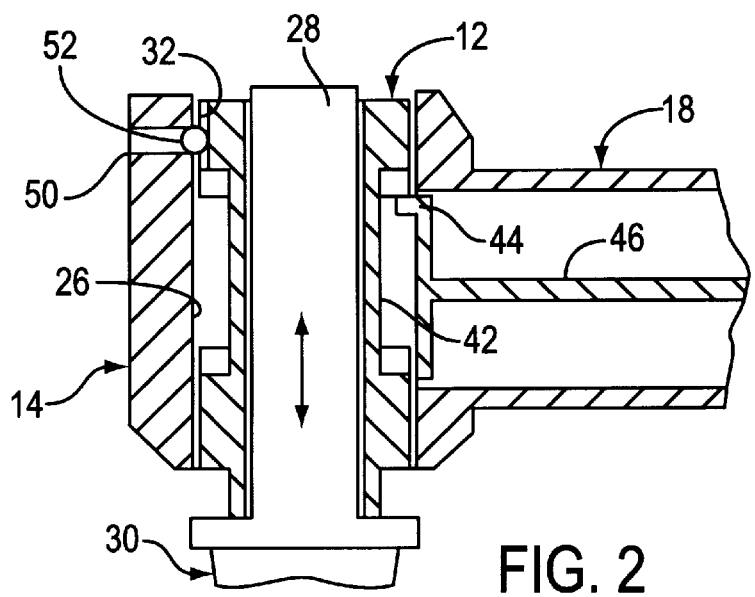
FIG. 2 is partial sectional view of the hand-piece and sleeve of FIG. 1 in an assembled state.
Figure 3:
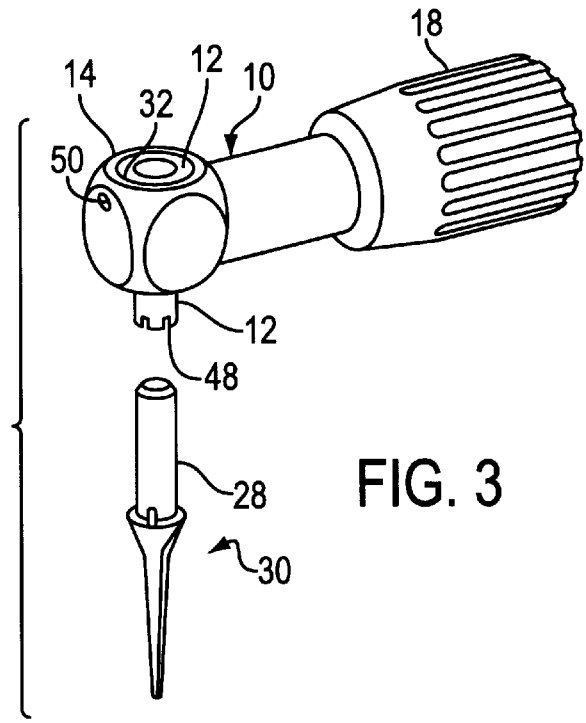
FIG. 3 is a partial exploded view in perspective of the device of FIGS. 1 and 2, illustrating connection of a tool.

The dental tool of the present invention is used and applied in combination with a conventional, commercially available drive head, or hand-piece, which is improved in accordance with the present invention. Such a drive head is assembled of conventional driving elements, which do not in themselves form a novel part of the present invention and thus are not illustrated or described in great detail. Reference is made to the issued U.S. Pat. No. 4,976,625 by the inventor here and the patents referenced therein. The hand-piece device is generally of a sufficiently slender and elongated nature, often having a contra-angle head, to enable a dentist to easily and without injury to a patient, manipulate the device within the mouth and, more particularly, against even the rear molars.

With reference to FIGS. 1–4, a hand-piece 10 holds a tool-holding sleeve 12 reciprocatingly within a head 14. Rotary motion of a driver mechanism 16, shown schematically in FIG. 1, acting through the hollow, elongated body 18 of the hand-piece 10 converts rotary motion into the desired reciprocating movement of the sleeve 12.

The sleeve 12 is generally cylindrical in shape and has two flanges 20,22 at the top and adjacent the bottom end. The sleeve 12 has an axial bore 24 with an internal sliding surface within which the shaft 28 of a tool 30 is held in use of the invention.

The upper and lower flanges 20,22 mate securely, but slidably within the head 14 of the hand-piece 10. A groove 32 in the outer surface 34 of the upper flange 20 extends between an upper surface 36 and a similar lower surface 38. The groove 32 is thus generally concentric about the axis 40 of the sleeve 12 but is oriented transversely to the axis 40 in a spiral-like manner.

The distance between the flanges 20, 22, that is, the height of the smaller diameter central portion 42, provides an annular recess and is sufficient to hold the full stroke of the eccentrically rotating drive member 44 (shown schematically in FIG. 1). The eccentric 44 is driven by a shaft mechanism 46 that extends inside the hollow body 18 of the hand-piece 10. The shape of the eccentric 44 and the length of the center portion 42 determine the axial stroke of the sleeve 12 and any tool 30 attached thereto.

A notched rim portion 48 on the sleeve 12 provides for engagement with a tool 30 in a manner that prevents rotation of the tool 30 relative to the sleeve 12. It should also be understood that the tool and sleeve may be constructed as a single integral component.

Embedded in the bore 50 and protruding beyond the sliding surface 26 within the head 14 is a steel ball 52. When the sleeve 12 is inserted within the head 14, the steel ball 52 rides within the groove 32. Thus, when the eccentric 44 induces periodic reciprocal motion in the sleeve 12 in the direction of the axis 40, a simultaneous periodic oscillatory motion around the axis 40 is also produced in the sleeve 12 as the ball 52 rides in the groove 32.

Assuming, to better describe operation, that the sleeve 12 reciprocates so that the steel ball 52 rides fully from one end of the groove 32 to the other end of the groove 32 and then returns to the starting point, then a point A on the groove will oscillate (FIG. 4) between points A and A', through an angle θ simultaneously with each full reciprocating cycle of the sleeve 12. The tool 30 that is fixed to the sleeve 12, of course, oscillates around the axis 40, and reciprocates simultaneously with the motion of the sleeve 12 in the direction of the axis 40.

The period of the reciprocating cycle is identical with the period of the oscillating cycle. The reciprocating position along the axis 40 of the sleeve 12 relative to time is controlled by the shape of the eccentric 44 and the dimensions of the center portion 42 of the sleeve 12.

The angular oscillating position of the sleeve 12 around the axis 40 at any time during the periodic cycle is determined by the contours of the groove 32 as it extends between the upper surface 36 and the lower surface 38 of the sleeve 12. The groove 32 may provide a direct connection as illustrated in FIG. 1. However, an infinite number of groove shapes are available. It is possible to select from many possible oscillatory motions, for example, whether rotation about the axis 40 is clockwise or counterclockwise when the sleeve 12 moves up (as seen in FIG. 1), dependent on the angular directions of the notch.

Rotation of the sleeve 12 about the axis 40 may be continuous, although not necessarily with constant angular velocity, as the sleeve reciprocates. On the other hand, as explained hereinafter, there may be no rotation about the axis 40, for example at the extremes, top and bottom, of the reciprocating cycle where the reciprocating direction reverses. Also, it is possible that the rotation about the axis 40 will pause or reverse itself during each half cycle of reciprocal motion. Thus, the simple translational reciprocating motion of a tool 30 in the U.S. Pat. No. 4,976,625 patent is improved with a compound motion that is a combination of controlled reciprocation and controlled oscillation relative to the sleeve axis 40.

For example, a dental saw cuts a larger channel because of reciprocal and oscillatory motion and therefore moves more easily, less binding, than a similar saw in accordance with U.S. Pat. No. 4,976,625. It is easier to pull a round saw out of the drilled hole.

It should be understood that in alternative embodiments in accordance with the invention, the groove 32 may be formed in the sliding surface 26 of the head 12 and a protrusion may be provided, for example, on the outer surface 34 of the sleeve 12 such that the eccentric drive 16 will produce the same reciprocatory/oscillatory motion for the sleeve 12 and its attached tool 30.

The methods and materials for constructing a dental tool 30 that is integral with the sleeve 12 are described in the U.S. Pat. No. 4,976,625 and these techniques are applicable for the improved constructions described herein.

Figure 5:
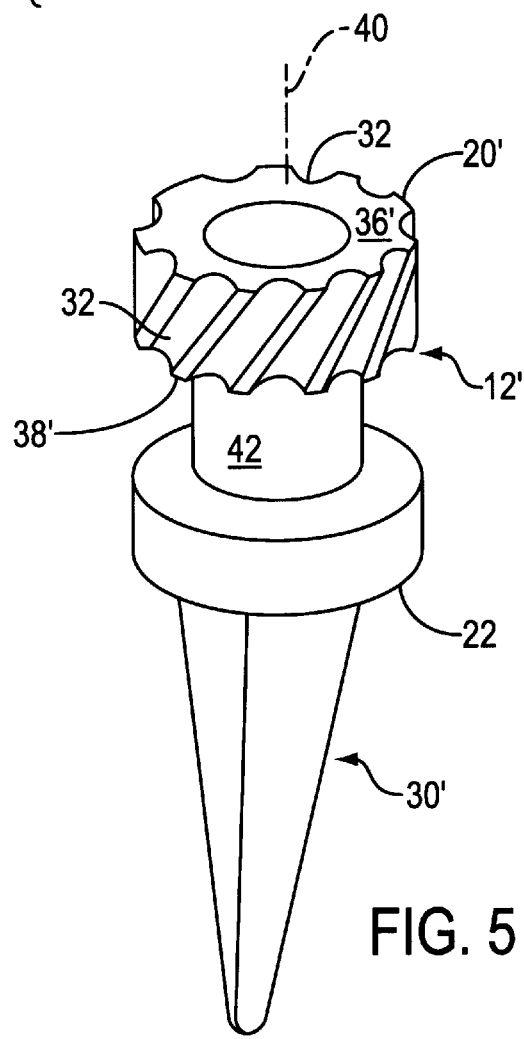
FIG. 5 is an alternative embodiment of a combination sleeve and tool in accordance with the invention.

In FIG. 5, a plurality of grooves 32 are located on the upper flange 20' extending between the upper annular surface 36' and the lower surface 38'. The grooves 32 may have any contour as discussed above with regard to FIGS. 1–4. When a tool 30' is not symmetrical around the longitudinal axis 40, the practitioner may have a preferred angular orientation for the tool 30' in the head 14. This preference is satisfied by engaging the steel ball 52 in the groove 32 that provides tool orientation closest to the practitioner's preference.

Figure 7:
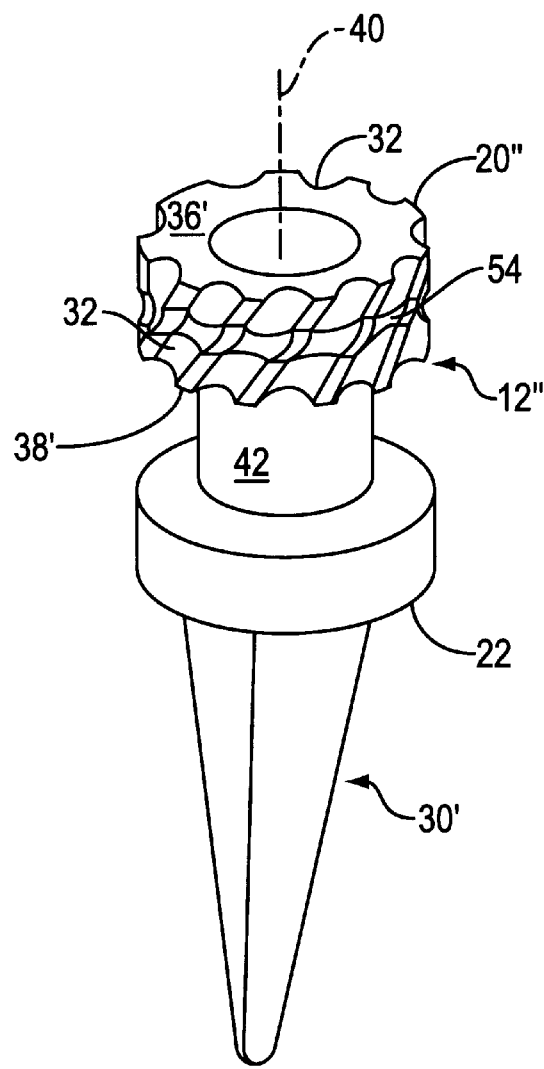
FIG. 7 is another alternative embodiment of a sleeve and tool combination in accordance with the invention.

In FIG. 7, the upper flange 20" includes a plurality of grooves 32 as in FIG. 5. However, the upper flange 20" is further split horizontally (as illustrated) by a circumferential channel 54 which is in a general plane perpendicular to the axis 40 and preferably is not as deep as the grooves 32. This construction permits rotation under stress of the tool 30' around the axis 40 and relative to the head 14 and ball 52. That is, movement of the ball 52 from one groove 32 to another can occur via the channel 54 and thereby the relative angle of the tool 30' in the head 14 is changed. This repositioning of the tool 30' may be done manually when the tool is not operating, or this repositioning may occur spontaneously when forces of the tool against the work-piece (tooth, prosthetic) exceed a high level which might otherwise cause jamming of the tool or injury to the work-piece.

Tools can be provided for insertion into dental interspaces, for example, for polishing, cleaning, abrading and shaping, or applying medication. By increasing the number of grooves 32, the angular relationship between the tool and the head can be more precisely controlled. In addition, by closer angular spacing of the grooves 32, there is also provided greater control over the releasing force, than for relatively thick walls between grooves 32. By varying the flexural modulus of the walls, that is by selecting a suitable material of construction, the release force for allowing the ball 52 to move from groove to groove via the channel 54 can be varied over a wide range, and a particular tool may be selected depending for example, on the age and health of a patient being treated and the treatment being given.

If the tool becomes lodged, and an excessive rotational moment is exerted, a relatively resilient material defining the grooves 32 on the flange 20" can flex and permit the steel ball 52 to escape the groove 32, permitting rotation of the tool and entry of the steel ball 52 into an adjacent groove 32, and preventing injury to the teeth. For this purpose, the material forming the notch wall should have a suitable flexural elastic modulus and thickness.

Figure 8:
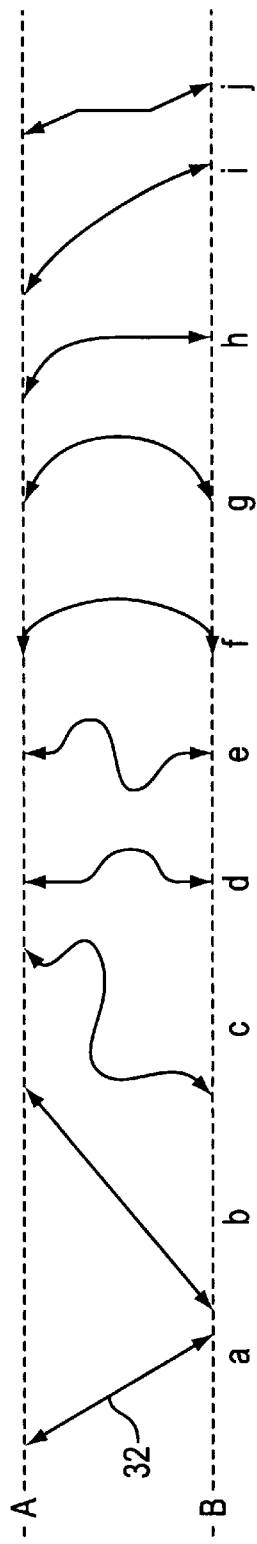
FIG. 8 is a diagram illustrating paths for oscillation of a tool in accordance with the invention.

Conceptually, the number of contours for the groove 32 are infinite for defining the oscillatory motion of the sleeve and attached tool. FIG. 8 demonstrates several possibilities. It should be kept in mind that the pathways, although illustrated in a plane, are actually wrapped concentrically spiral-like about the axis 40, as described above. FIG. 8 shows the path which the steel ball 52 would follow during a reciprocation cycle of the tool 30 while travelling from a position A to a position B. At the left in FIG. 8 is a general representation of the groove 32 illustrated in FIG. 1. At b there is a similar motion that starts in the opposite direction resulting in tool rotation in opposite directions. The oscillatory excursion is greater at b than at a. At c, the sloped path includes a sine-type wave. At d, the oscillatory excursion occurs at the middle of the reciprocal stroke, but the end points of the oscillatory motion are the same as in the 625 patent, i.e. only axial reciprocation. At e is a sine-type wave that returns to the starting point many times in one cycle of reciprocation. At f an elliptical path is illustrated, and at g, a semicircular path is illustrated. At h, the oscillation occurs only in two ¼ portions of a reciprocal cycle. Curve i is intended to represent any of the many possible curved paths between points A and B. Groove j provides a pause (no oscillatory motion) at the midpoint of each reciprocatory stroke.

As stated, the conceptual paths are limitless in number. From a practical view, production methods, available materials, speed of operation and differing wear for differently shaped grooves, will limit the choices.

It should be understood that the grooves 32 on a single sleeve may have different contours, one from the other, whereby the practitioner may select from the available motions and during his work may change the motion without fully removing the sleeve and its connected tool from the head of the hand-piece.

Figure 9:
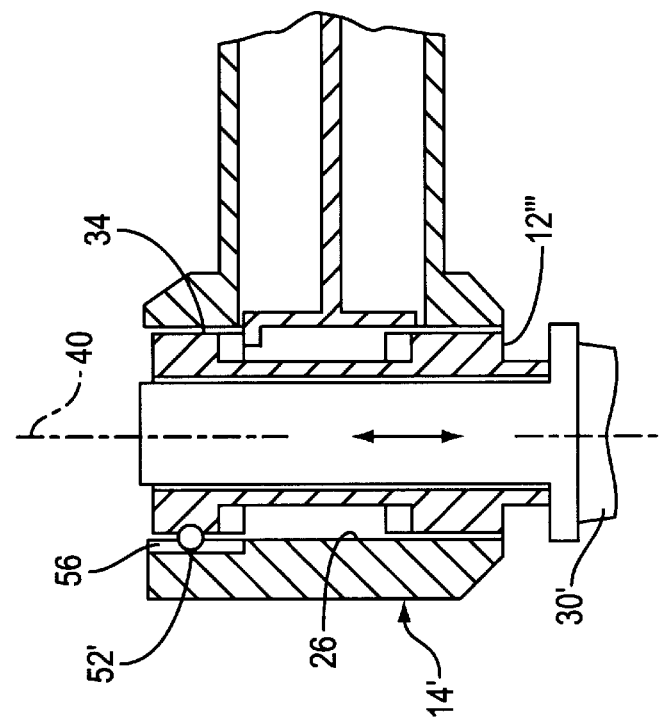
FIG. 9 is a view similar to FIG. 2 of another alternative embodiment in accordance with the invention of a dental hand-piece in section.

FIG. 9 illustrates an alternative embodiment in accordance with the invention of a construction where a protrusion 52' extends from the sleeve surface 34 to engage a groove 56 on the inner sliding surface 26 of the head 14'. When the groove 56 is not axial, that is, when it is wrapped on the surface so as to be concentric about the reciprocating axis 40, eccentric driving of the sleeve will produce both reciprocating and oscillating motion for the sleeve and its attached tool.

Figure 6:
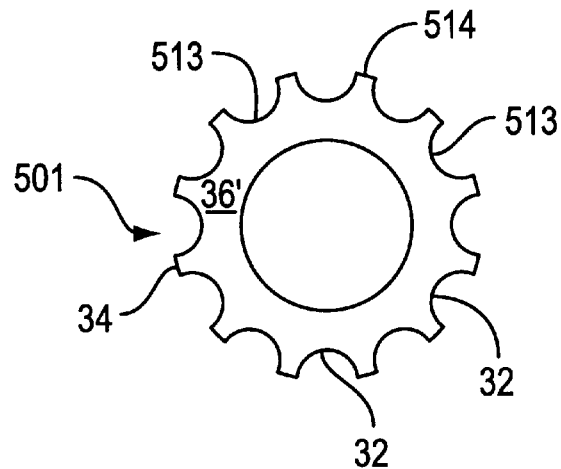
FIG. 6 is a top view of the embodiment of FIG. 5.

Multiple equi-spaced grooves 56 may be provided on the surface 26 and a "horizontal" channel 58 (not shown) in the surface 26 may connect the grooves 56 to achieve the advantages of the embodiments of FIGS. 6 and 7.

Figure 10:
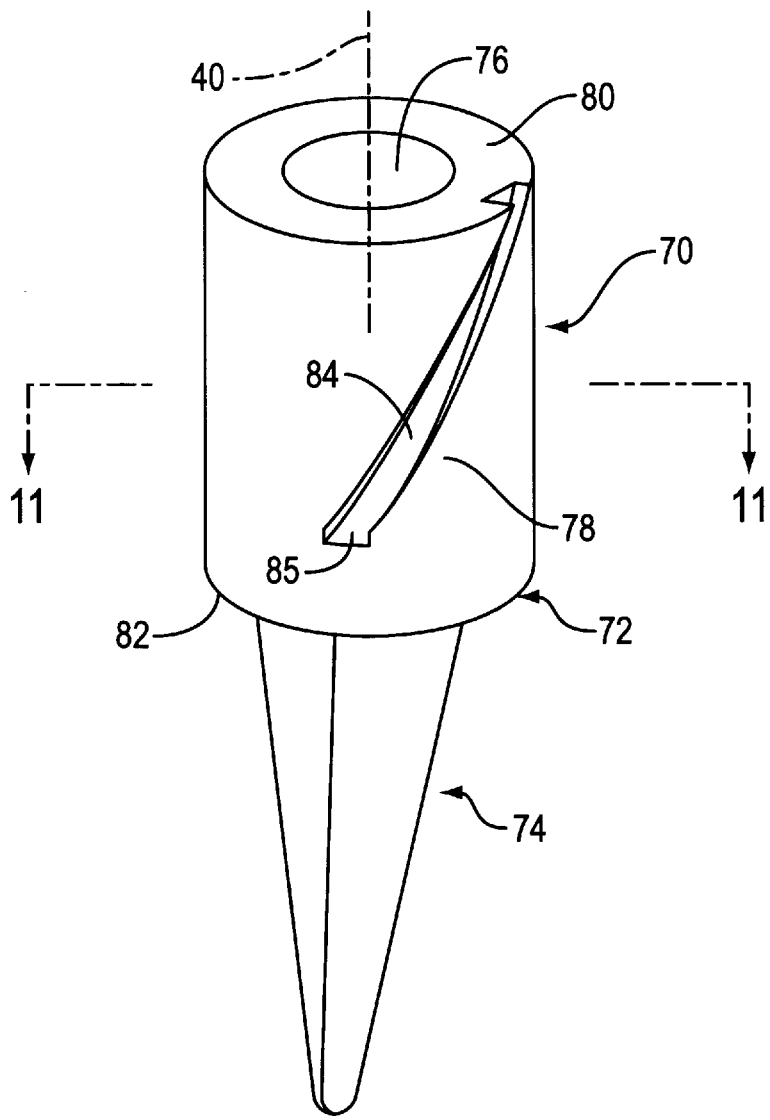
FIG. 10 is a front top perspective view, similar to FIG. 5, of another alternative embodiment in accordance with the invention.
Figure 11:
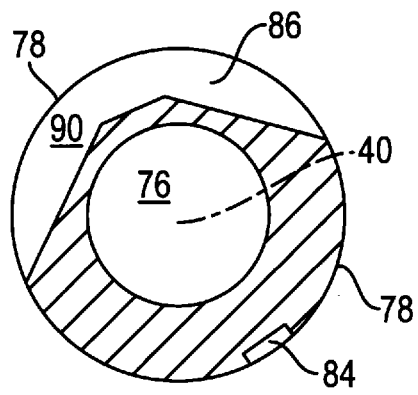
FIG. 11 is a sectional view taken along the line 11—11 of FIG. 10.
Figure 12:
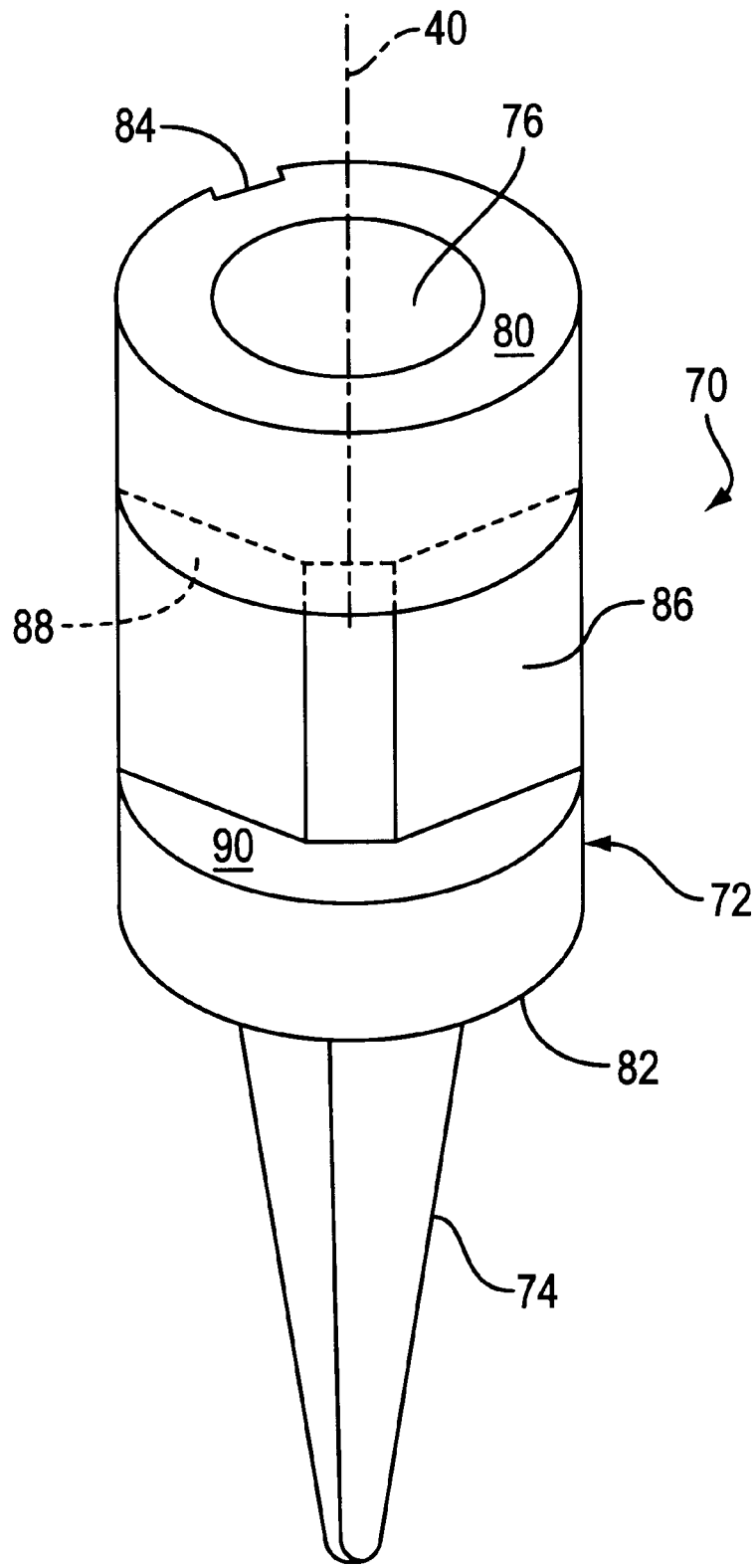
FIG. 12 is a rear top perspective view of the embodiment of FIG. 10.

FIGS. 10–12 illustrate another alternative embodiment of a sleeve construction in accordance with the invention. The sleeve 70 includes a generally cylindrical shaft 72 to which a tool 74 is attached. As in the other illustrated embodiments, a bore 76, aligned with the sleeve axis 40, in the shaft 72 receives a replaceable tool 74. Alternatively, the tool 74 and the sleeve 70 may be an integral component. The outer cylindrical surface 78 of the sleeve 70 extends from an upper annular surface 80 to a lower annular surface 82.

A groove 84 extends into the outer cylindrical surface 78 from the upper annular surface 80 toward the lower surface 82 in a path that is concentric with the longitudinal axis 40. That is, portions of the groove 84 are oriented transversely to the axis 40, as described above. The end 85 of the groove 84 closest to the tool 74 terminates within the shaft 72. The many contours that are possible for the groove 84 (as described above) determine the oscillating aspects of the tool motion during operation.

The cross-section of the groove 84 is illustrated as generally rectangular. This differs from the generally semicircular groove illustrated in the prior embodiments. It should be understood that the cross-section of the groove 84 (and in the other embodiments) may be of any suitable shape so long as the protrusion (for example, 52 in FIG. 2) is correspondingly shaped for entry and snug fit in the groove 84.

A slot 86 is recessed in the shaft 72 at a circumferential portion of the cylindrical outer surface 78 that is generally opposite to the groove 84. The slot 86 is defined by an upper surface 88 and a lower surface 90. The eccentric element 44 in the hand-piece 10 (FIG. 1) acts between the surfaces 88 and 90 to provide the desired reciprocating motion of the sleeve 70. Thus, the center portion of the sleeve 70 between the surfaces 88, 90 is not cylindrical as in the other embodiments described above.

It should be understood that a modification (not shown) of the sleeve 70 may provide a protrusion from the outer cylindrical surface 78 that engages a groove located in the sliding surface 26 of the head 14', as illustrated, for example, in FIG. 9.

The embodiment in accordance with the invention of FIGS. 10–12 has the advantages that the groove 84 can be much longer in the axial direction and thereby produce for the same axial length of the sleeve a greater reciprocating stroke than in the previous embodiments. A larger angle θ of oscillation (FIG. 4) is also possible, if desired.

Further, in the embodiment of FIGS. 10–12, the area of the bearing surface, that is, the outer surface 78 for contact with the sliding surface 26 of the head 14, is substantially greater. Thus, with the same machining precision, the sleeve of FIGS. 10–12, reciprocates and oscillates in the head, with less slack or tendency to wobble or bind therein. Terminating the groove 84 within the shaft 72 (at 85) reduces the possibility of malfunction that may occur should the protrusion in the head 14 escape from the groove 84 during operation.

Use of a rectangular cross-section for the groove 84 also may provide a better fit and more controlled oscillatory motion. A self-centering V-shaped notch and corresponding protrusion (not shown) may also be used to advantage as compared with a rounded protrusion and rounded groove.

A relative disadvantage of the embodiment of FIGS. 10–12 is that the number of grooves 84 that may be placed in the outer cylindrical surface 78 is limited to a circumferential area with an arc of approximately 180°. Thus, the advantages of the configurations of FIGS. 5 and 7, where grooves are spaced around an entire 360° periphery are limited in the embodiment of FIGS. 10–12.

It should be understood that the drive mechanism to produce reciprocal motion of the sleeve need not be limited to the mechanical arrangement suggested herein. Other concepts may be applied, for example, pneumatic, hydraulic, electromagnetic, mechanical, to provide reciprocal motion.

It will thus be seen that the objects set forth above and those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

What is claimed is:

1. A dental sleeve for sliding on a generally cylindrical sliding surface provided on the head of a dental hand-piece, said sleeve comprising:

a longitudinal axis and a mating surface generally cylindrical and concentric about the longitudinal axis, said sleeve being combinable with said hand-piece with said mating surface slidingly engaged with said sliding surface of said hand-piece;

at least one elongated groove in said mating surface, each said groove for facing said sliding surface and extending in length to define a path from a respective first point on said mating surface to a respective second point on said mating surface, said first and second points being axially spaced apart in the direction of said longitudinal axis, at least a portion of each said path between said first and second points being transverse to said longitudinal axis; and means for receiving driving forces that produce reciprocal motion of said sleeve along said axis.

2. A dental sleeve as in claim 1, wherein said means for receiving forces include a first flange and a second flange on said sleeve and spaced axially apart, an eccentrically driven element being receivable between said flanges to cause said reciprocal motion of said sleeve along said axis.

3. A dental sleeve as in claim 2, wherein said first flange has axial thickness and includes said mating surface with said at least one groove in said mating surface.

4. A dental sleeve as in claim 1, wherein there is a plurality of said grooves spaced about a circumference of said mating surface, and further comprising a circular channel in said mating surface at a right angle with said axis, and located between said respective first and second points.

5. A dental sleeve as in claim 4, wherein said grooves are deeper than said channel.

6. A dental sleeve as in claim 1, wherein at least another portion of each said path is parallel to said axis to produce a pause in oscillatory motion of said sleeve when in use in the head of said dental hand-piece.

7. A dental sleeve as in claim 1, wherein there is a plurality of said grooves spaced about a circumference of said mating surface, a path from the respective first point to the respective second point of at least one said groove being different from a path from the respective first point to the respective second point of another of said at least one groove.

8. A dental sleeve as in claim 1, wherein said sleeve oscillates about said axis concurrently with reciprocal motion along said axis.

9. A dental sleeve as in claim 1, wherein said means for receiving forces include a slot on said sleeve, said slot having opposed surfaces transverse to said axis and spaced axially apart, an eccentrically driven element being receivable between said transverse surfaces to cause said reciprocal motion of said sleeve along said axis.

10. A dental sleeve as in claim 9, wherein said at least one groove and said slot are positioned in opposed circumferential halves of said generally cylindrical mating surface.

11. A dental sleeve as in claim 9, wherein said mating surface has a first longitudinal end and a second longitudinal end, said at least one groove having said first point at said first longitudinal end and said second point being spaced from said second longitudinal end.

12. A dental sleeve as in claim 1, wherein said at least one groove is one of curved, rectangular and V-shaped in cross-section.

13. A dental hand-piece, comprising:

a head having an internal cylindrical sliding surface concentric with a longitudinal axis;

a sleeve having a mating surface generally cylindrical and concentric with said longitudinal axis, said mating surface being slidingly engaged with said internal sliding surface of said head;

at least one elongated groove in one of said mating surface and said sliding surface, each said groove facing said engaged surface and extending in length to define a path from a respective first point to a respective second point, said first and second points being axially spaced apart in the direction of said longitudinal axis, at least a portion of each said path between said first and second points being transverse to said longitudinal axis;

a protrusion extending from the other of said mating surface and said sliding surface and engaged in one of said at least one groove; and means for receiving driving forces that produce reciprocal motion of said sleeve in said head.

14. A dental hand-piece as in claim 13, wherein said means for receiving forces include a first flange and a second flange on said sleeve and spaced axially apart, an eccentrically driven element being receivable between said flanges to cause said reciprocal motion of said sleeve along said axis.

15. A dental hand-piece as in claim 14, wherein said first flange has axial thickness and includes said mating surface.

16. A dental hand-piece as in claim 13, wherein there is a plurality of said grooves spaced about a circumference of one of said mating surface and said sliding surface, and further comprising a circular channel in said grooved surface, said channel being at a right angle with said axis, and located between said respective first and second points.

17. A dental hand-piece as in claim 16, wherein said grooves are deeper than said channel.

18. A dental hand-piece as in claim 13, wherein at least another portion of each said path is parallel to said axis to produce a pause in oscillatory motion of said sleeve when in use in the head of said dental hand-piece.

19. A dental hand-piece as in claim 13, wherein there is a plurality of said grooves spaced about a circumference of said mating surface, a path from the respective first point to the respective second point of at least one said groove being different from a path from the respective first point to the respective second point of another of said at least one groove.

20. A dental hand-piece as in claim 13, wherein said sleeve oscillates about said axis concurrently with reciprocal motion along said axis.

21. A dental hand-piece as in claim 13, wherein said means for receiving forces include a slot on said sleeve, said slot having opposed surfaces transverse to said axis and spaced axially apart, an eccentrically driven element being receivable between said transverse surfaces to cause said reciprocal motion of said sleeve along said axis.

22. A dental sleeve as in claim 21, wherein said at least one groove and said slot are positioned in opposed circumferential halves of said generally cylindrical mating surface.

23. A dental hand-piece as in claim 21, wherein said mating surface and said sliding surface each has a respective first longitudinal end and a second longitudinal end, said at least one groove having said first point at said first longitudinal end of an associated surface and said second point being spaced from said second longitudinal end of the associated surface.

* * * * *